United States Patent [19]

Schwenke et al.

[11] Patent Number: 5,077,766
[45] Date of Patent: Dec. 31, 1991

[54] METHOD AND ARRANGEMENT FOR ANALYZING SPECIMENS PURSUANT TO THE X-RAY FLUORESCENCE ANALYSIS METHOD

[75] Inventors: Heinrich Schwenke, Escheburg; Joachim Knoth, Hamburg; Harald Schneider, Geesthacht; Ulrich Weisbrod, Hamburg; Herbert Rosomm, Geesthacht, all of Fed. Rep. of Germany

[73] Assignee: CKSS Forschungszentrum Geesthacht GmbH, Geesthacht, Fed. Rep. of Germany

[21] Appl. No.: 518,724

[22] Filed: Dec. 1, 1989

[30] Foreign Application Priority Data

Dec. 2, 1988 [DE] Fed. Rep. of Germany ....... 3840590

[51] Int. Cl.⁵ .......................................... G01N 23/223
[52] U.S. Cl. ...................................... 378/45; 378/44; 378/50
[58] Field of Search .................. 378/44, 45, 42, 53, 378/54, 70, 71, 84, 85, 73, 76, 189, 190, 50

[56] References Cited

U.S. PATENT DOCUMENTS 4,426,717 1/1984 Schwenke et al. ................. 378/45
4,785,470 11/1988 Wood et al. ....................... 378/45

Primary Examiner—Janice A. Howell
Assistant Examiner—Don Wong
Attorney, Agent, or Firm—Robert W. Becker & Associates

[57] ABSTRACT

A method and arrangement for analyzing specimens pursuant to the X-ray fluorescence analysis method utilizing a beam detector to detect a secondary beam that originates from the specimen that is to be analyzed and upon which is directed a primary X-ray beam, the path of which is adjustable in at least one axis of freedom. The surface of a specimen holder on which the specimen is placed is disposed parallel to, and at a defined distance from, a reference plane at which the primary beam is reflected under total reflection conditions. Subsequently, the path of the primary beam is adjusted relative to the reference plane while simultaneously detecting, with a detector, the radiation spectrum of the secondary beam of the specimen. At a predetermined energy level of the primary beam, a secondary beam intensity maximum, to which is assigned a specific reference angle, is determined.

21 Claims, 4 Drawing Sheets

METHOD AND ARRANGEMENT FOR ANALYZING SPECIMENS PURSUANT TO THE X-RAY FLUORESCENCE ANALYSIS METHOD

BACKGROUND OF THE INVENTION

The present invention relates to a method and arrangement for analyzing samples or specimens pursuant to the X-ray fluorescence analysis method utilizing a beam detector to detect a secondary beam that originates from the specimen that is to be analyzed and upon which is directed a primary X-ray beam, the path of which is adjustable in at least one axis of freedom.

With one known apparatus (German Patent 36 06 748), the primary beam of an X-ray tube is glancingly guided at an angle of only a few minutes onto the surface of the sample that is to be analyzed, with the adjustment of the effective angle of incidence being undertaken by altering the height of the X-ray tube relative to the specimen that is to be analyzed. An orifice plate inserted directly in the path of the beam after the X-ray tube limits the divergence of the primary beam emitted thereby.

Basically, applicable for this known apparatus as well as in general, upon glancing incidence of X-ray beams onto a planar surface, the primary X-ray beam penetrates only slightly vertically into the body below the surface. For an angle of incidence below the critical or limiting angle of the total reflection, the depth of penetration is even limited to only a very few mm. This known effect makes arrangements for measuring the characteristic fluorescent radiation (secondary radiation or beam) upon glancing incidence of the primary radiation principally into a potentially suitable instrument for determining elements in layers close to the surface. Furthermore, such an effect could also be used for the X-ray fluorescence analysis of extremely small specimens of the order of magnitude of $\mu g$, for example dust or residue from solvents, whereby the specimens are placed upon planar polished surfaces that then serve as specimen holders. With such a use, the effect that originates from the surface below the specimen holder, and that under total reflection conditions is extremely low, leads to detection limits of an order of magnitude of pg.

The two uses of the total reflection effect in X-ray fluorescence analysis, in other words not only the analysis of layers near the surface but also the extreme trace analysis of specimens that are placed upon suitable specimen holders, place considerable demands on the technical configuration of total reflection arrangements.

These high demands result from the opposing requirements for a high primary beam intensity (small distance between X-ray tube and the specimen that is to be analyzed) and a high precision of the angular setting (greater distance between X-ray tube and specimen). Due to the physical principle that underlies an X-ray tube, with X-ray tubes that are available today it is merely possible to achieve a primary beam intensity that is very low in comparison to the synchrotron radiation that can be achieved with large accelerators. Already for this reason, it is cogent, when using X-ray tubes as radiation sources for such arrangements, to keep the distances between the anodes thereof and the object that is to be analyzed as low as possible to minimize spacial angle losses.

Furthermore, it has been shown to be advantageous, rather than directing the X-ray beam directly onto the specimen, to indirectly direct the X-ray beam onto the specimen after deflecting the beam via a totally reflecting surface. However, such an arrangement, such as the one disclosed in Schwenke et al U.S. Pat. No. 4,426,717, issued Jan. 17, 1984, limits the adjustability of the angle of incidence upon the specimen in such a way that it cannot be used for the analysis of surfaces that require that the angle of incidence be freely adjustable over a wide range.

It is therefore an object of the present invention to provide a method of analyzing specimens pursuant to the X-ray fluorescence analysis method of the aforementioned general type, with the inventive method making it possible to determine the angle of incidence of the primary beam upon the specimen with a greater precision than was previously possible, whereby any desired angle of incidence of the primary beam upon the surface of the specimen can be set exactly and the angle of incidence of the primary beam can be measured absolutely.

It is another object of the present invention to provide an arrangement for X-ray fluorescence analysis whereby, while maintaining minimal distances between the X-ray tube and the specimen that is to be analyzed, a free adjustability, without affecting one another, of the angle of incidence of the primary beams upon the mirror as well as upon the specimen can be provided with straightforward means, whereby angular adjustments with a precision of up to 0.1 mrd should be capable of being achieved, and the apparatus should be straightforward in construction and hence economical to provide.

BRIEF DESCRIPTION OF THE DRAWINGS

These and other objects and advantages of the present invention will appear more clearly from the following specification in conjunction with the accompanying schematic drawings, in which.

SUMMARY OF THE INVENTION

Figure 1:
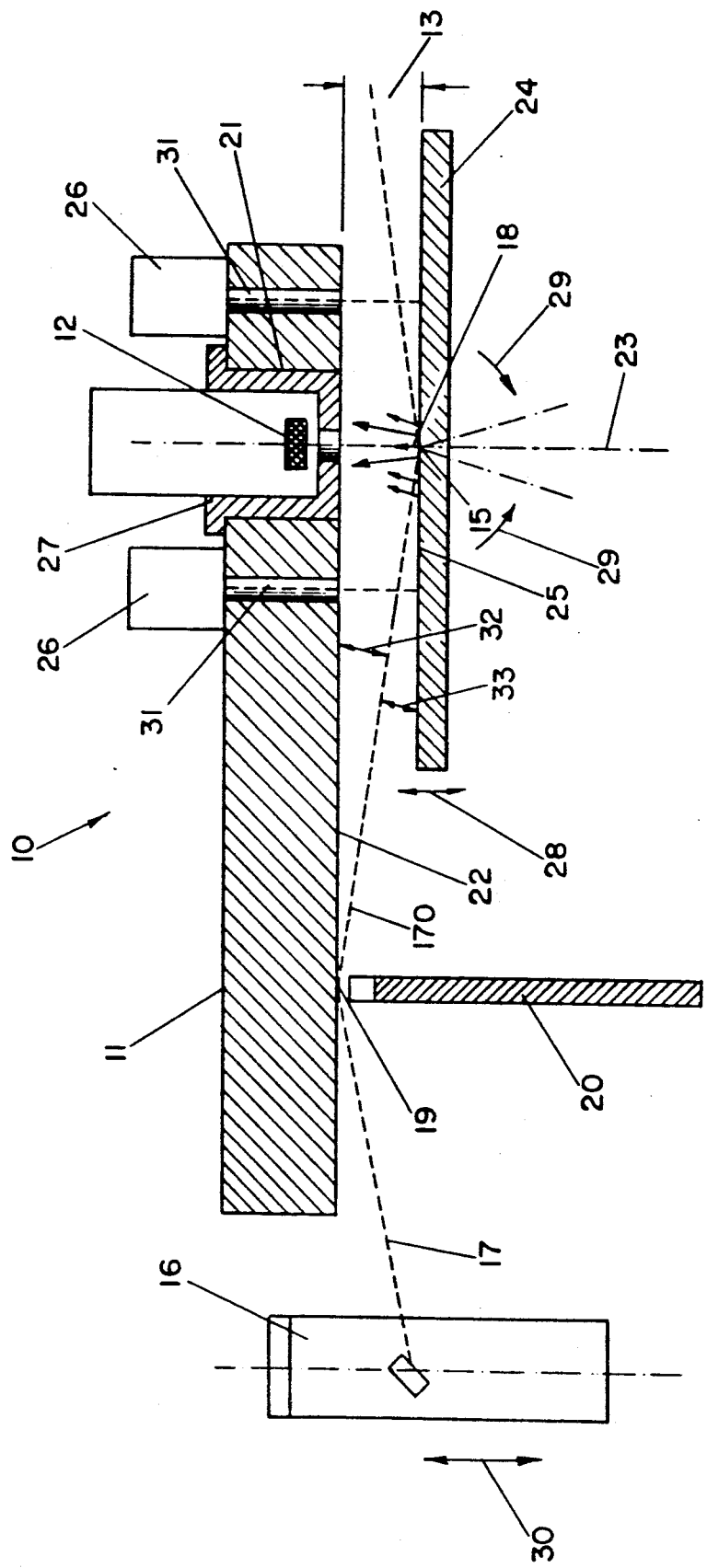
FIG. 1 is a partially cross-sectioned side view of one exemplary embodiment of the inventive arrangement showing cooperating components, with the path of the primary beam being schematically illustrated.

The method of the present invention is characterized primarily by the steps of: disposing the specimen on a specimen holder; placing the surface of the specimen holder on which the specimen is disposed parallel to, and at a defined distance from, a reference plane at which the primary X-ray beam is reflected under total reflection conditions; subsequently adjusting the path of the primary beam relative to the reference plane while simultaneously detecting, with the beam detector, the radiation spectrum of the secondary beam of the specimen that is disposed on the surface of the specimen holder; and at a predetermined energy level of the primary beam, determining a secondary beam intensity maximum, to which is assigned a specific reference angle.

The advantage of the inventive method is essentially that with it the problem or angular measurement that is central to the total reflection X-ray fluorescence spectroscopy is resolved in an optimum manner. In addition, with the inventive method it is possible to advantageously exactly and automatically set any desired angle of incidence of the primary beam upon the surface of the specimen.

Pursuant to one advantageous specific embodiment of the inventive method, any desired angle of incidence at which the primary X-ray beam reflected at the reference plane strikes the surface of the specimen can be adjusted relative to the reference angle.

The inventive arrangement for analyzing a specimen pursuant to the X-ray fluorescence analysis method, and which includes a carrier member on which is disposed a beam detector to determine a secondary beam that originates from the specimen that is to be analyzed, and which also includes an X-ray radiation source, which is adjustable relative to the carrier member and emits a primary beam that during the analysis process is directed onto the specimen, is characterized primarily in that the carrier member is provided with a reflection zone for reflecting the primary beam coming from the X-ray radiation source under total reflection conditions.

The advantage of the inventive approach consists primarily in that the angle at the carrier member, which acts as a quasi mirror, can be utilized in order, via the specific energy/angular relationship of the reflection coefficients of the X-ray beam, to affect the energy spectrum of the primary beam independently of the angle of incidence upon the specimen.

The specimen is held at an exactly defined distance (order of magnitude of about $10^{-4}$ m) relative to the carrier member, so that the beam reflected at the carrier member strikes the specimen.

This can advantageously be further enhanced if the reflection zone of the primary beam on the carrier member is configured in such a way as to be vertically and/or horizontally focusing, for example in the form of a curvature of the reflection surface.

Pursuant to another advantageous specific embodiment of the inventive arrangement, by means of an orifice plate, which is disposed on the carrier member essentially in the reflection zone of the primary beam, the direct components of the primary beam are kept away from the site of the specimen. This assures that the specimen that is to be analyzed will be excited by only the primary beam that is reflected at the reflection surface of the carrier member under total reflection conditions. The orifice plate is advantageously embodied as a barrier orifice plate, and in particular has a slot width of 1 to $5 \times 10^{-5}$ m.

The carrier member, which is advantageously embodied as a parallelepipedal block, is provided with a hole that traverses the same at essentially right angles to a reference plane of the primary beam, with the detector being disposed in this hole. With this embodiment of the present invention, the carrier member assumes not only the function of a mirror for the primary beam that originates from the X-ray radiation source (X-ray reflector), but also assumes the function of a reference device (optical bank) with which the orifice plate and the specimen that is to be analyzed can be coordinated. Up to now, this double function required a plurality of separate components that in addition had to b mounted and adjusted separately, accompanied by the inherent number of possibilities for errors.

Pursuant to another advantageous specific embodiment of the inventive arrangement, the detector is surrounded by an orifice plate that can be formed about the detector in the manner of a cylindrical orifice plate. Such an orifice plate keeps undesired primary and secondary radiation away from the detector and defines that portion of the specimen that it is desired to analyze by limiting the respectively undesired fluorescent radiation field that comes from the other portions of the specimen.

Although in principle a specimen or a specimen holder having a specimen can be disposed below the detector, i.e. below a region about a receiving axis of the detector, it is advantageous to dispose an exchangeable specimen carrier essentially centrally relative to the receiving axis of the detector, with this axis extending essentially perpendicular to the reference plane; this specimen carrier is advantageously adjustable axially and/or angularly relative to the receiving axis of the detector. In this manner, the angle of incidence of the primary beam, which is reflected at the carrier member, onto the specimen can be varied independently of the angle of reflection at the carrier member; this is of great practical significance since not only the angle of reflection at the carrier member but also the angle of incidence must frequently be set pursuant to different criteria, i.e. the angle at the carrier member is used for the aforementioned special energy/angle relationship of the coefficient of reflection of the X-ray beam, while the angle of incidence onto the specimen determines the depth of penetration of the primary beam into the specimen.

In particular for a very precise and/or automatic measurement process, where a highly precise automatic specimen positioning is final, the distance between the reference plane of the carrier member and a surface of a specimen that is supported by the specimen holder is detected by gap-detecting means. In this way, the distance can be set very precisely and it is not necessary to press the specimen that is to be analyzed against the carrier member.

The gap-detecting means is preferably formed by a measuring device that delivers an evaluatable physical value in conformity with the distance between the carrier member and the surface of the specimen. The measured value can be conveyed directly to adjustment members that adjust the specimen carrier, or the specimens disposed thereon, at a desired distance and angle relative to the detector, i.e. to the receiving axis thereof.

In particular for a desired very precise automatic positioning of the specimen, it is advantageous to embody the measuring device in such a way that the distance between the reflection surface and the surface of the specimen can be detected without having to make contact.

Regardless of the construction of the gap-detecting means, it is now possible by providing such means to set any positioning of the specimen or of the specimen holder having surfaces with a diameter of up to 15 cm. Due to the high degree of positioning precision that can be achieved with the present invention, it is possible without limitation to use specimen changers, and it is also possible without limitation to analyze large specimens.

Pursuant to one advantageous specific embodiment of the inventive arrangement, the carrier member, at least in the reflection zone, is coated with an alternating cyclical sequence of a plurality of individual layers of metal and nonmetal. Multilayer coatings of this type are also designated SMLS coatings (SMLS=Synthetic Multilayer Structure), with these SMLS structures involving known layer structures with which, pursuant to the present invention, upon reflection on such coatings, a band-pass-filtration is possible with which a large selectivity and steepness or width of transition interval is possible and hence a very precise angular measurement is possible. Thus, by providing this SMLS coating in the reflection zone, the measurement precision of the inventive method and arrangement are considerably improved and increased even further.

With regard to the construction of the individual layers, it is advantageous to use tungsten and/or platinum as the metal, and carbon and/or silicon and/or a metal silicide or silicate as the nonmetal. The number of layers forming the overall coating is at least 20–200, with the thickness of the layers being in the neighborhood of $10^{-9}$ m, i e. in the order of magnitude of nanometers.

Further specific features of the present invention will be described in detail subsequently.

DESCRIPTION OF PREFERRED EMBODIMENTS

Referring now to the drawings in detail, the arrangement 10 (see in particular FIG. 1) essentially comprises a carrier member 11 in the form of a parallelepipedal block, and an X-ray radiation source 16, the shiftability of which is indicated by the arrow 30. However, it should be understood that this shiftability of the x-ray radiation source 16 in the direction of the arrow 30 is intended to be only a symbolic representation. In fact, the X-ray radiation source 16 is embodied in such a way that it can be shifted or pivoted relative to the carrier member 11 in all axes of freedom. Provided in the carrier member 11, at a distance from the X-ray radiation source 16, is a hole 21 that extends through the carrier member 11 at essentially right angles to the basically planar underside of the carrier member. The reflection zone 19 for the primary beam 17 on the carrier member 11 is extended by the underside of the carrier member to a reference plane 22 for the surface of the specimen. Disposed in the hole 21, as part of the arrangement 10, is the beam detector 12. The detector is provided with a receiving axis 23 that extends at right angles to the surface of reflection 22 of the primary beam 17, 170. As seen with the arrangement of FIGS. 1 and 2, a replaceable specimen holder 24 is disposed centrally relative to the receiving axis 23 of the detector, and is also disposed below the reflection surface or plane 22. As shown by the arrows 28 and 29, the specimen holder 24 can be pivoted axially and at an angle relative to the receiving axis 23 of the detector.

Positioned on the specimen holder 24 is a sample or specimen 15 that is to be analyzed with this being symbolically shown by the arrows that are directed in the direction toward the beam detector 12 and that indicate the secondary beam 18 (fluorescent radiation) that originates from the specimen 15.

Figure 2:
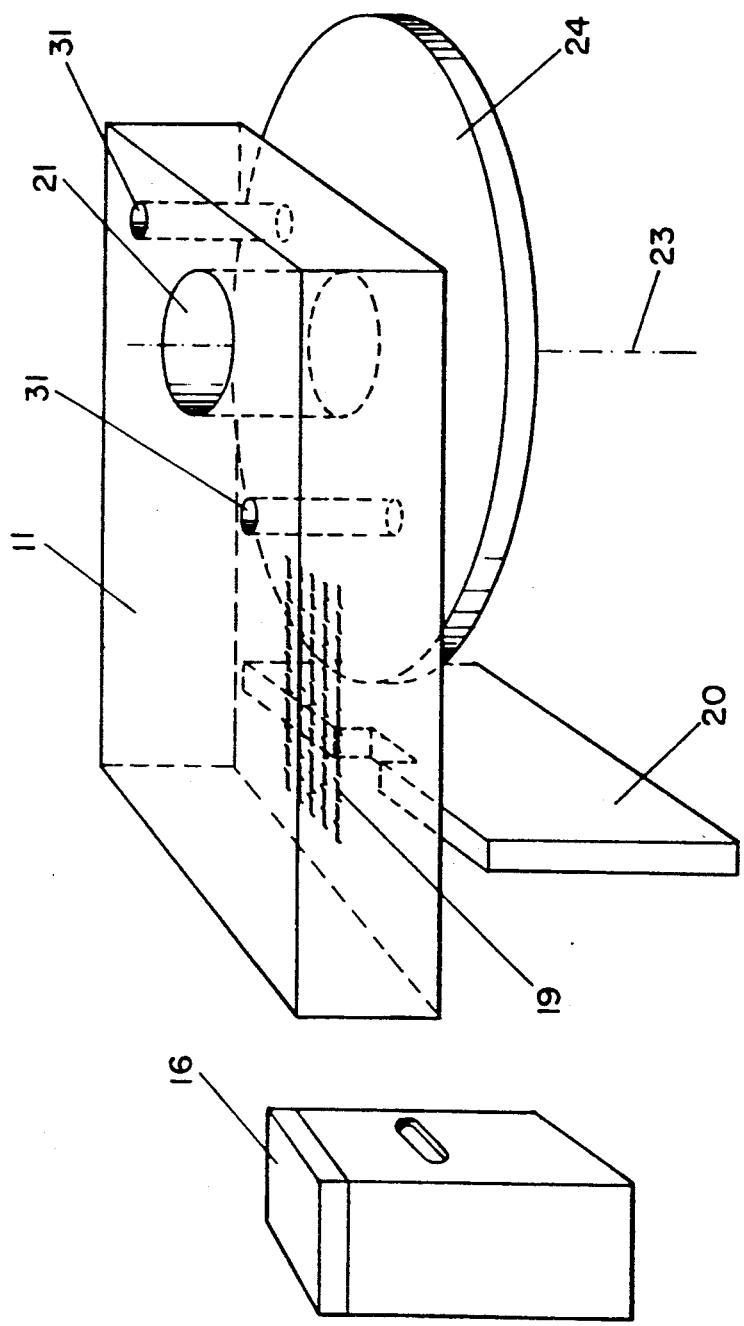
FIG. 2 is a perspective view of the principal structure of the arrangement of FIG. 1, with individual components being partially omitted.
Figure 3:
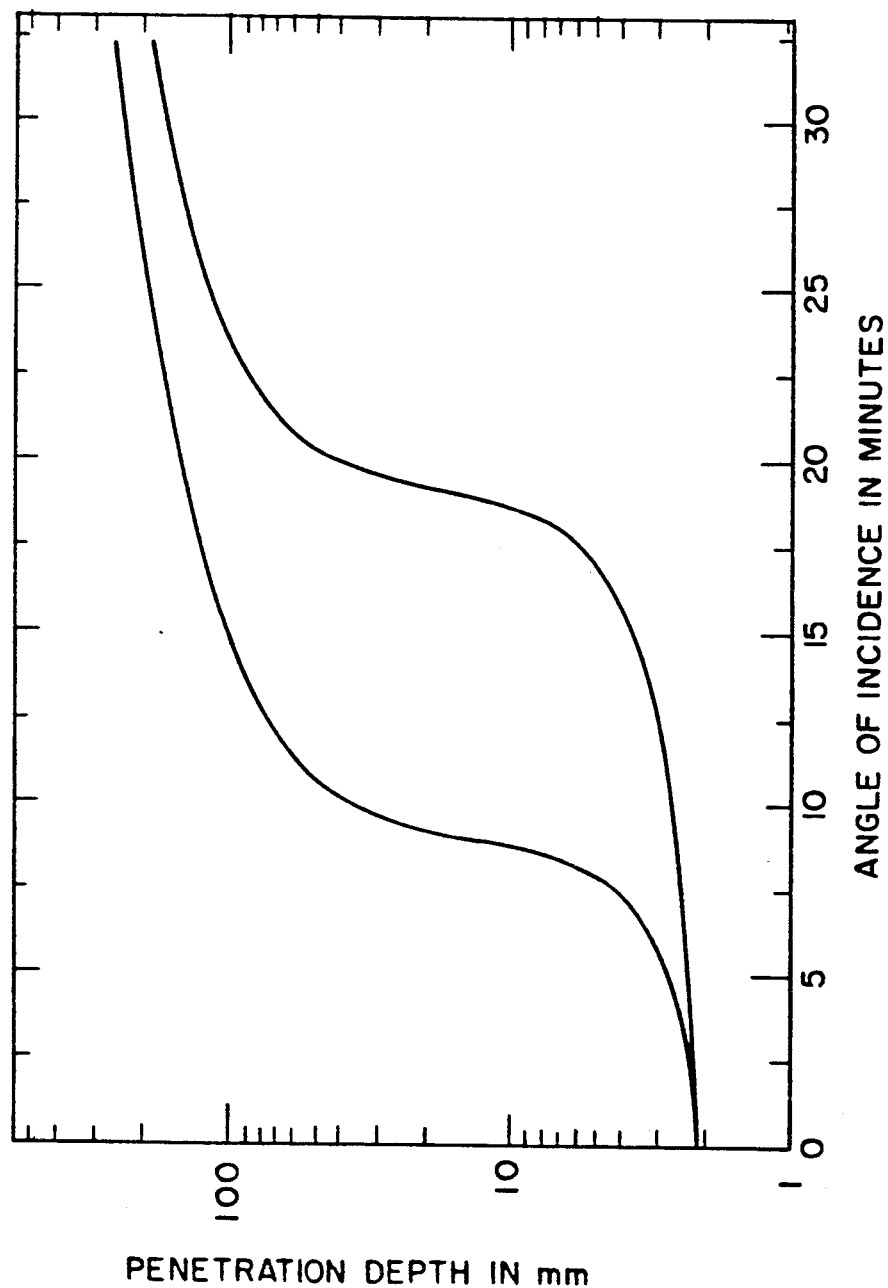
FIG. 3 is a graph in which the penetration depth of the primary beam is plotted as a function of the angle of incidence for two different primary energies under total reflection conditions.

Above the reference plane 22, when observing the illustration of FIGS. 1 and 2, at least one gap-detecting means 26 is disposed on the carrier member 11, which is embodied as a parallelepipedal block. At that location where a respective gap-detecting means 26 is disposed on the carrier member 11, a through bore 31 traverses the carrier member 11, with this through bore extending essentially parallel to the receiving axis 23 of the detector. The space or gap 13 between the reference plane 22 of the carrier member 11 and a surface 25 of a specimen 15 supported by the specimen holder 24 can thus be detected by the gap-detecting means 26. This gap-detecting means can, for example, be formed by a measuring device that is provided with measuring probes, so that an evaluatable physical value in conformity with the gap 13 between the carrier member 11 and the surface 25 of the specimen 15 is provided by having, for example, the measuring probes directly contact the surface 25 of the specimen 15 or the specimen holder 24, and be moved toward or away from the gap-detecting means 26 by displacement.

Furthermore, although not shown in detail, the measuring device could detect the gap between the reference plane 22 and the surface 25 of the specimen 15 without making contact.

Finally, the arrangement 10 includes orifice plates 20, 27, with the orifice plate 20 being disposed on the carrier member 11 essentially in the reflection zone 19 of the primary beam 17. The orifice plate 20 is embodied as a barrier orifice plate. The slot width of the orifice plate 20 is, for example, 1 to $5 \times 10^{-5}$ m. The orifice plate 20 is disposed approximately halfway between the anodes of the tubes of the X-ray radiation source 16 and the specimen 15. The width of the slot can, for example, be adjusted by spacers relative to the reflection zone 19 of the carrier member 11.

Disposed about the beam detector 12 is the aforementioned second orifice plate 27, which is preferably in the form of a cylindrical orifice plate. This cylindrical orifice plate additionally keeps undesired primary and secondary beams from the beam detector 12 and defines the portion of the sheet-like specimen 15 that is to be analyzed by limiting the field of the secondary fluorescent beam 18.

The path of the primary beam 17, 170 is illustrated by the dotted line that originates from the X-ray radiation source 16, is reflected at the carrier member 11 in the reflection zone 19 under total reflection conditions, and then arrives at the specimen 15 as the reflected primary beam 170.

The carrier member 11 is preferably made of a quartz glass or of metal, although in principle any suitable material can be used to form the carrier member. For example, it is also possible to make the carrier member 11 of, for example, quartz glass, and to metallically coat the reflection plane 22.

The carrier member 11 is preferably coated in the reflection zone 19 with an alternating cyclical sequence of a plurality of individual layers of metal or nonmetal. The coating formed by the plurality of layers is in general indicated as an SMLS coating (SMLS=Synthetic Multilayer Structure). The individual metal layers of the overall coating can, for example, contain tungsten and/or platinum, whereas the nonmetal layers can, for example, be formed by carbon and/or silicon and/or a metal silicide or silicate. The number of layers can be arbitrarily varied, but is preferably from 20 to 200, with the thickness of the layers being approximately $10^{-9}$ m.

Figure 4:
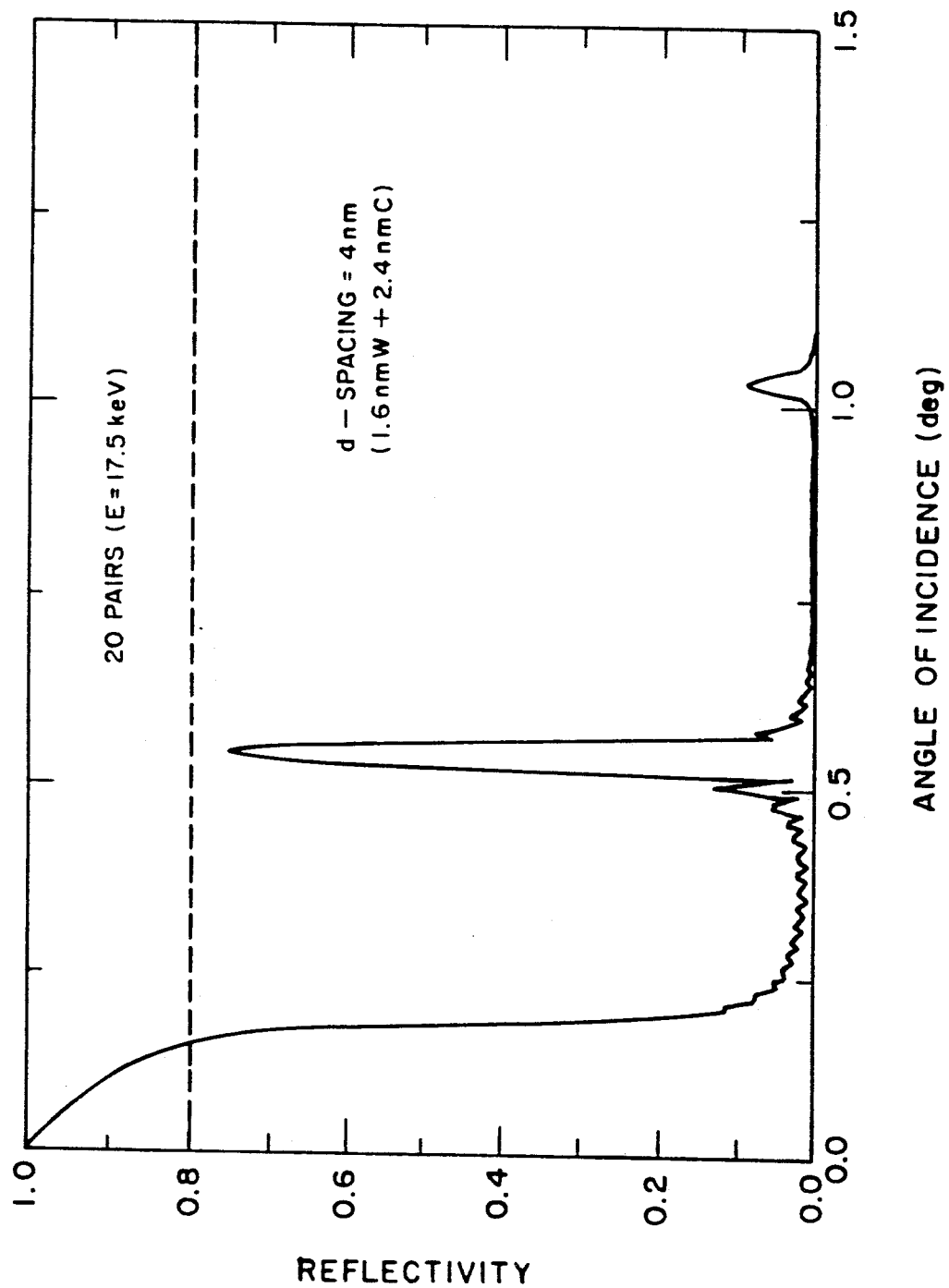
FIG. 4 shows the relationship between the intensity of the secondary beam that is detected by a detector and the set reference desires at a predetermined energy of the primary beam, with an intensity maximum of the secondary beam being assigned to a specific reference angle.

As shown in FIG. 4, in contrast to reflection surfaces (reflection zone 19) that have not been optimized in the aforementioned manner, with a reflection on SMLS coatings, an angle analysis utilizing the band-pass-filtration on the SMLS coatings is possible, with this angle analysis utilizing the very high selectivity and the steepness or width of transition interval, which was previously not possible and leads to a considerable increase in the precision of the measurement.

The method that can be carried out with the inventive arrangement 10 has the following sequence of steps:

First of all, the specimen 15 is disposed on the surface of the specimen holder 24. The surface 25 of the probe is then placed parallel to and at a defined distance 13 from the reference plane 22, at which the primary X-ray beam 17 is reflected under total reflection conditions in the reflection zone 19 and, as the reflected beam 170, strikes the surface 25 of the specimen 15 that is disposed on the specimen holder 24. Thereafter, the path of the primary beam 17 that originates from the X-ray radiation source 16 is varied relative to the reference plane 22 (see FIG. 1), and in particular in the direction of the arrow 30. As a result, the angle of reflection 32 between the reference plane 22 and the path of the reflected primary beam 170 is varied. At the same time, the radiation spectrum of the secondary beam 18 of the specimen 15 that is disposed on the surface of the specimen holder 24 is detected by the beam detector 12, and in particular in such a way that subsequently, at a predetermined energy level of the primary beam 17, a secondary beam intensity maximum is determined, and in particular utilizing known relationships between the angle of reflection 32 and the intensity of the reflected primary beam 170, so that the specific angle of reflection can be associated with the secondary beam intensity maximum.

In so doing, any desired angle of incidence 33 at which the primary beam 17 that is reflected at the reference plane 22 strikes the surface 25 of the specimen can be set relative to the determined reference angle.

It should be noted that the specimen holder 24 can itself be the specimen 15 that is to be examined, such as, for example, if the specimen holder 24 is a semiconductor wafer that is to be analyzed. The specimen 15 is then, for example, a structure that is to be analyzed in or below the surface 25 of the specimen, i.e. the surface 25 of the specimen holder.

The present invention is, of course, in no way restricted to the specific disclosure of the specification and drawings, but also encompasses any modifications within the scope of the appended claims.

What we claim is:

1. In a method of analyzing a specimen pursuant to an X-ray fluorescence analysis method utilizing a beam detector to detect a secondary beam that originates from the specimen to be analyzed and upon which specimen is directed a primary X-ray beam, the path of which is adjustable in at least one direction, the improvement including the steps of:

disposing said specimen on a specimen holder;

placing the surface of said specimen holder on which said specimen is disposed parallel to, and at a variably selectable distance from, a reference plane at which said primary X-ray beam is reflected under total reflection conditions;

subsequently varying the path of said primary X-ray beam relative to said reference plane while simultaneously detecting, with said beam detector, the radiation spectrum of said secondary beam of said specimen that is disposed on said surface of said specimen holder as a function of varying said path of said primary beam; and at a predetermined energy level of said primary X-ray beam, determining a secondary beam intensity maximum, to which is assigned a specific reference angle.

2. A method according to claim 1, in which any desired angle of incidence at which said primary X-ray beam that is reflected at said reference plane strikes said surface of said specimen holder is adjustable relative to said reference angle.

3. In an arrangement for analyzing a specimen pursuant to an X-ray fluorescence analysis method, including a carrier member on which is disposed a beam detector to determine a secondary beam that originates from said specimen to be analyzed and including an X-ray radiation source, which is adjustable relative to said carrier member for emitting a primary beam that during an analysis process is directed onto said specimen, the improvement wherein:

said carrier member is provided with a reflection zone for reflecting said primary beam coming from said X-ray radiation source under total reflection conditions.

4. An arrangement according to claim 3, in which said reflection zone is extended via an underside of said carrier member to form a reference plane for a surface of said specimen.

5. An arrangement according to claim 4, in which said reflection zone for said primary X-ray beam on said carrier member is embodied to be vertically and/or horizontally focusing.

6. An arrangement according to claim 4, which includes a first orifice plate disposed on said carrier member essentially in said reflection zone of said primary X-ray beam.

7. An arrangement according to claim 6, in which said orifice plate is a barrier orifice plate.

8. An arrangement according to claim 7, in which said barrier orifice plate has a slot width of 1 to $5 \times 10^{-5}$ m.

9. An arrangement according to claim 4, in which said carrier member is in the form of a parallelepipedal block having a hole that traverses said carrier member essentially at right angles to said reference plane, with said detector being disposed in said hole.

10. An arrangement according to claim 9, in which said detector is surrounded by a second orifice plate.

11. An arrangement according to claim 4, in which said beam detector has a receiving axis extending essentially at right angles to said reference plane; and in which a replaceable specimen holder is disposed essentially concentrically relative to said receiving axis below said beam detector.

12. An arrangement according to claim 11, in which said specimen holder is axially and angularly adjustable relative to said receiving axis of said detector.

13. An arrangement according to claim 11, which includes a gap-detecting means for detecting a gap between a surface of a specimen supported by said specimen holder, and said reference plane of said carrier member.

14. An arrangement according to claim 13, in which said gap-detecting means is in the form of a measuring device that delivers an evaluatable physical value that corresponds to said gap between said carrier member and said surface of said specimen.

15. An arrangement according to claim 14, in which said measuring device is provided with a detecting means that detects said gap between said reference plane and said surface of said specimen in a contact-less manner.

16. An arrangement according to claim 3, in which said carrier member is made of quartz glass.

17. An arrangement according to claim 3, in which said carrier member is made of metal.

18. An arrangement according to claim 3, in which said carrier member is provided with a metallic coating, at least in said reflection zone.

19. An arrangement according to claim 3, in which said carrier member is provided at least in said reflection zone with a coating comprising a alternating cyclical sequence of a plurality of individual layers of metal and nonmetal.

20. An arrangement according to claim 19, in which said metal is selected from at least one of the group consisting of tungsten and platinum, and said nonmetal is selected from at least one of the group consisting of carbon, silicon, metal silicide, and metal silicate.

21. An arrangement according to claim 19, which includes at least 20–200 layers having a thickness in the neighborhood of $10^{-9}$ m.

* * * * *

UNITED STATES PATENT AND TRADEMARK OFFICE
CERTIFICATE OF CORRECTION

PATENT NO.   :   5,077,766

DATED        :   Dec. 31, 1991

INVENTOR(S)  :   Schwenke et al

It is certified that error appears in the above-identified patent and that said Letters Patent is hereby corrected as shown below:

On the title page;
[73] Assignee:   GKSS Forschungszentrum Geesthacht GmbH, Geesthacht, Fed. Rep. of Germany Signed and Sealed this Nineteenth Day of January, 1993

*Attest:*

DOUGLAS B. COMER

*Attesting Officer*     Acting Commissioner of Patents and Trademarks